(12) United States Patent
Hur et al.

(10) Patent No.: US 11,255,833 B2
(45) Date of Patent: Feb. 22, 2022

(54) GAS DETECTION DEVICE

(71) Applicant: HONEYWELL INTERNATIONAL INC., Morris Plains, NJ (US)

(72) Inventors: Sang-Hoon Hur, Seoul (KR); Jae-Hwan Lee, Seoul (KR); Je-Phil Ahn, Seoul (KR)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 95 days.

(21) Appl. No.: 16/134,308

(22) Filed: Sep. 18, 2018

(65) Prior Publication Data
US 2019/0086379 A1    Mar. 21, 2019

(30) Foreign Application Priority Data
Sep. 19, 2017 (KR) .......................... 10-2017-0120286

(51) Int. Cl.
*G01N 33/00* (2006.01)
*H05K 5/03* (2006.01)
*G08C 19/00* (2006.01)
*G01N 1/24* (2006.01)

(52) U.S. Cl.
CPC ..... *G01N 33/0063* (2013.01); *G01N 33/0027* (2013.01); *G08C 19/00* (2013.01); *H05K 5/03* (2013.01); *G01N 1/24* (2013.01)

(58) Field of Classification Search
CPC .. G01N 33/0063; G01N 33/0027; G01N 1/24; G01N 33/0009; G01N 33/0031; G01N 33/0032; H05K 5/03; G08C 19/00; G01D 11/24; G01D 11/245; G01D 11/26

USPC .............. 73/31.05, 23.2–31.07, 431, 863.83, 73/864.34; 340/632–634
See application file for complete search history.

(56) References Cited

U.S. PATENT DOCUMENTS

| 7,841,224 B2 * | 11/2010 | Son .................... G01N 33/4972 73/1.02 |
| D734,187 S | 7/2015 | Nakajima |
| 2003/0046975 A1 * | 3/2003 | Wewers ............. G01N 33/0016 73/23.21 |
| 2006/0010974 A1 * | 1/2006 | Koyano ............. G01N 33/0009 73/431 |

(Continued)

FOREIGN PATENT DOCUMENTS

| JP | 2002-324283 A | 11/2002 |
| JP | 2009-244075 A | 10/2009 |

(Continued)

OTHER PUBLICATIONS

Decision to Grant issued in Korean Application No. 10-2017-0120286 on Feb. 26, 2019, 3 pages.

(Continued)

*Primary Examiner* — Robert R Raevis
(74) *Attorney, Agent, or Firm* — Alston & Bird LLP

(57) ABSTRACT

A gas detection device comprises a pump module for drawing in air; a sensor module including a plurality of unit sensors detecting a gas included in the air; a driving module driving the pump module and the sensor module; and a case including a main body mounted to allow at least one among the pump module, the sensor module, and the driving module to be detachable and a cover connected to the main body to allow the at least one among the pump module, the sensor module, and the driving module to be exposed.

19 Claims, 23 Drawing Sheets

(56) References Cited

U.S. PATENT DOCUMENTS

| | | | |
|---|---|---|---|
| 2006/0188407 A1* | 8/2006 | Gable | A61B 5/150992 |
| | | | 604/19 |
| 2010/0102959 A1 | 4/2010 | Ashrafzadeh et al. | |
| 2011/0048107 A1* | 3/2011 | Schulten | G01N 33/0014 |
| | | | 73/28.04 |
| 2018/0172625 A1* | 6/2018 | Ichikawa | G01N 27/41 |

FOREIGN PATENT DOCUMENTS

| | | |
|---|---|---|
| JP | 2010-092167 A | 4/2010 |
| KR | 10-2016-0078274 A | 7/2016 |
| KR | 10-2016-0137230 A | 11/2016 |

OTHER PUBLICATIONS

First Office Action issued in Korean Application No. 10-2017-0120286 dated Sep. 17, 2018, 13 pages.
Korean Design Patent Application No. 30-2017-0040227, published Apr. 5, 2018.
Notice of Allowance and Fees Due (PTOL-85) dated Jan. 17, 2019 for U.S. Appl. No. 29/638,749.
Registered European Community Design No. 004731297-0001, published Mar. 14, 2018, 6 pages.
Second Office Action issued in Korean Application No. 10-2017-0120286 dated Jan. 7, 2019, 8 pages.

* cited by examiner

US 11,255,833 B2

GAS DETECTION DEVICE

RELATED APPLICATION

This application claims priority of Korean Patent Application No. 10-2017-0120286 filed on Sep. 19, 2017, which is hereby incorporated herein by reference.

BACKGROUND

The present disclosure relates to a gas detection device.

Various gases may be used in semiconductor process lines and industrial sites, and gas detection devices may be operated to prevent large-scale accidents due to gas leaks. Gas detection devices may be used to detect gas in a chamber in which a semiconductor process is performed, or a gas pipe or a valve connected to such a chamber. Alternatively, gas detection devices may be used to detect a gas leak at industrial sites. Generally, various kinds of gases can be used in the field, therefore, there is an increasing demand for gas detecting apparatus being capable of detecting various kinds of gases.

SUMMARY

An aspect of the present disclosure provides a gas detection device capable of simultaneously detecting different gases and allowing for efficient maintenance in such a manner that a sensor detecting a gas and a pump determining a flow rate of air flowing into the gas detection device are modularized to be simply replaced, without additional equipment.

According to an aspect of the present disclosure, a gas detection device comprises a pump module for drawing in air; a sensor module including a plurality of unit sensors detecting a gas included in the air; a driving module driving the pump module and the sensor module; and a case including a main body in which at least one among the pump module, the sensor module, and the driving module is mounted to be detachable and a cover connected to the main body to allow the at least one among the pump module, the sensor module, and the driving module to be exposed.

According to an aspect of the present disclosure, a gas detection device comprises a case including a main body having a first accommodation space and a second accommodation space and a cover rotatably connected to the main body to allow the first accommodation space and the second accommodation space to be opened and closed; a pump module mounted in the first accommodation space to be slidably detachable and insertable and drawing in air; a sensor module mounted in the second accommodation space to be slidably detachable and insertable and detecting a gas included in the air; and a driving module provided on a rear of the first accommodation space and the second accommodation space and driving the pump module and the sensor module.

BRIEF DESCRIPTION OF DRAWINGS

The above and other aspects, features, and advantages of the present disclosure will be more clearly understood from the following detailed description when taken in conjunction with the accompanying drawings, in which.

DETAILED DESCRIPTION

Hereinafter, exemplary embodiments in the present disclosure will be described with reference to the attached drawings.

The contents of the present disclosure described below may have a variety of configurations and propose only a required configuration herein, but are not limited thereto.

Figure 1A:
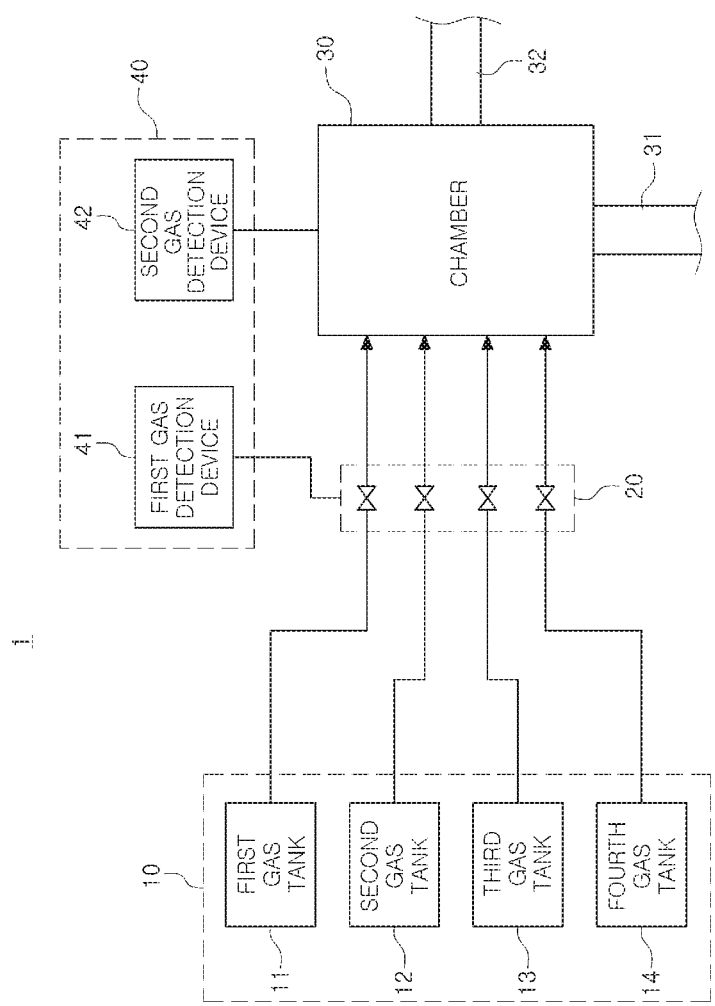
FIGS. 1a and 1b are schematic views of a processing apparatus including a gas detection device according to an exemplary embodiment.
Figure 1B:
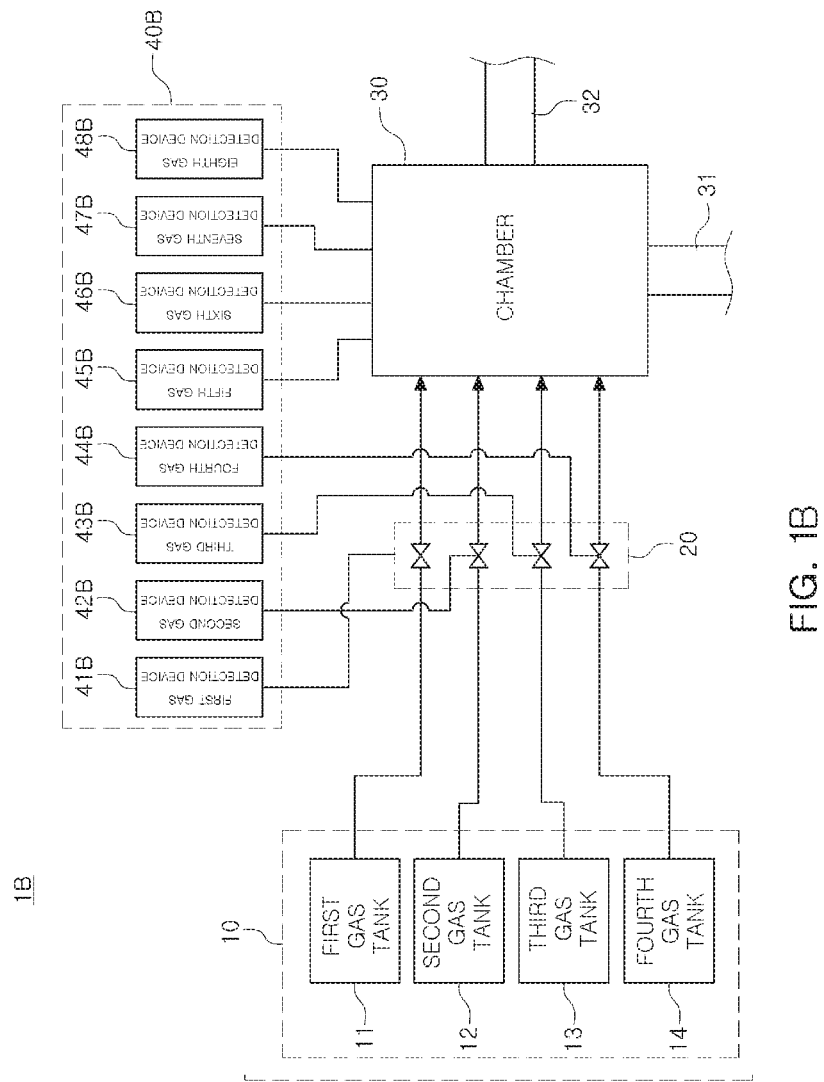

FIGS. 1a and 1b are schematic views of a processing apparatus including a gas detection device according to an exemplary embodiment.

With reference to FIG. 1a, a processing apparatus 1A according to an exemplary embodiment in the present disclosure may include a gas supply source 10, a valve 20, a chamber 30, and a gas detection device 40A. In an exemplary embodiment, the chamber 30 may be provided as a semiconductor process apparatus in which a semiconductor process, such as an etching process, a deposition process, photolithography, or a cleaning process, is performed. The chamber 30 may be connected to transport paths 31 and 32, transporting a substrate in which a semiconductor process is performed and may receive gases required for the process from the gas supply source 10.

The gas supply source 10 may include first to fourth gas tanks 11 to 14, storing different gases. In an exemplary embodiment illustrated in FIG. 1a, a case in which a total of four gas tanks 11 to 14 are included in the gas supply source 10 is taken as an example; however, this is merely an exemplary embodiment. A greater or smaller number of gas tanks may be included in the gas supply source 10. Gases stored in the first to fourth gas tanks 11 to 14 may be supplied to the chamber 30 using an operation of the valve 20.

In an exemplary embodiment illustrated in FIG. 1a, the gas detection device 40A may include a first gas detection device 41A and a second gas detection device 42A. The first gas detection device 41A may be connected to the valve 20 to determine whether a gas supplied to the valve 20 from the first to fourth gas tanks 11 to 14 has leaked. In the meantime, the second gas detection device 42A may be connected to the chamber 30 to detect a concentration of each of different gases present in the chamber 30 or to determine whether a gas has leaked outwardly of the chamber 30. That is, in an exemplary embodiment, both of the first gas detection device 41A and the second gas detection device 41B can sense the leakage of each of different gases.

In contrast, in an exemplary embodiment illustrated in FIG. 1*b*, a processing apparatus 1B may include first to fourth gas detection devices 41B to 44B connected to the valve 20, and fifth to eighth gas detection devices 45B to 48B can sense the leakage of gases in the chamber 30. Each of the first to eighth gas detection devices 41B to 48B can sense only one kind of gas. For example, the first gas detection device 41B and the fifth gas detection device 45B can sense the same kind of gas, which is stored in the first gas tank 11 and supplied to the chamber 30 through the valve 20.

The processing apparatus 1B may include a larger number of gas detection devices than the processing apparatus 1A, therefore, a large amount of manpower, time, and cost may be required for maintenance and repair. In an exemplary embodiment, each of the gas detection devices 41A and 42A can sense different kinds of gases, therefore, it is possible to save manpower, time, cost, and the like required for maintenance and repair.

Figure 2:
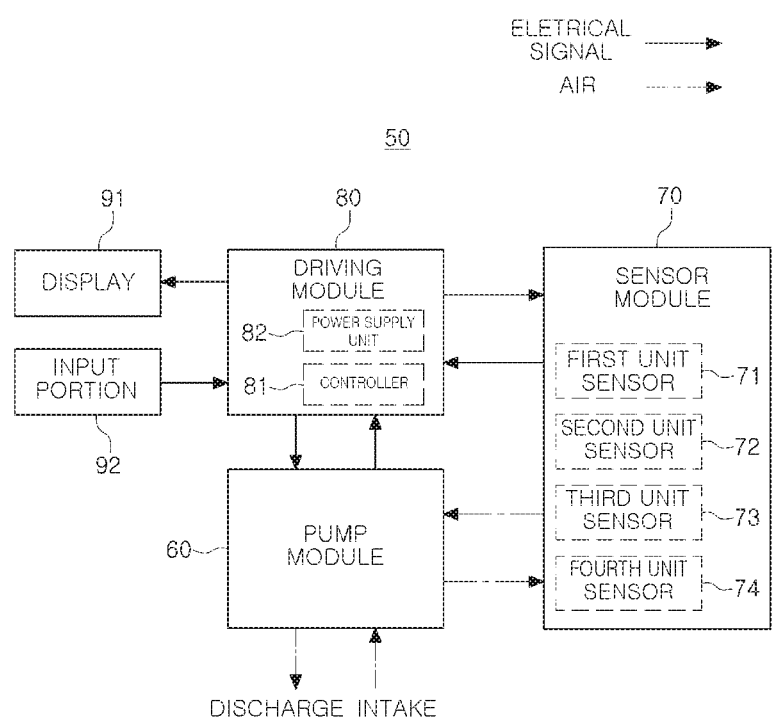
FIG. 2 is a schematic block diagram of a gas detection device according to an exemplary embodiment.

FIG. 2 is a schematic block diagram of a gas detection device according to an exemplary embodiment.

With reference to FIG. 2, a gas detection device 50 according to an exemplary embodiment may include a pump module 60, a sensor module 70, a driving module 80, and the like. The pump module 60 may include a pump for drawing in air to be supplied to the sensor module 70, as well as a flow rate sensor for measuring an amount of introduced air. The pump module 60 may be connected to ports provided in a case of the gas detection device 50 and may draw in and discharge air. In addition, the pump module 60 may supply air to the sensor module 70 through a path provided in the gas detection device 50. For the sake of understanding, the path of the air and the path of the electric signal are shown separately, in FIG. 2.

The sensor module 70 may include a plurality of unit sensors 71 to 74 for detecting gases included in air drawn in and supplied by the pump module 60. In an exemplary embodiment, the sensor module 70 may include first to fourth unit sensors 71 to 74, while the number of unit sensors 71 to 74 may be variously changed. Each of the unit sensors 71 to 74 may detect carbon monoxide, hydrogen, ammonia, hydrogen phosphate, and the like. In other words, each of the unit sensors 71 to 74 may detect different gases.

The driving module 80 may supply power required for an operation of the pump module 60 and the sensor module 70 and may control the operation thereof. The driving module 80 may include a controller 81, a power supply unit 82, and the like. The driving module 80 may display a type and a concentration of a gas detected by the sensor module 70 on a display 91 or may monitor an operational state of the pump module 60 and the sensor module 70 to display whether the pump module 60 and the sensor module 70 malfunction, on the display 91. In the meantime, a user may transmit a command to control an operation of the gas detection device 50 to the driving module 80 through an input portion 92.

The gas detection device 50, according to an exemplary embodiment, may include the pump module 60, the sensor module 70, the driving module 80, and the like, that have been modularized. The pump module 60 and the sensor module 70, requiring relatively frequent replacement and inspection, as compared with the driving module 80, may be disposed adjacent to a cover that is movable in a hinged manner or in a sliding manner. A user may open a cover of the gas detection device 50 and remove the pump module 60 and the sensor module 70 for inspection, or may easily replace the pump module 60 and the sensor module 70 with new products. Thus, it is possible to support efficient maintenance of the gas detection device 50.

Figure 3:
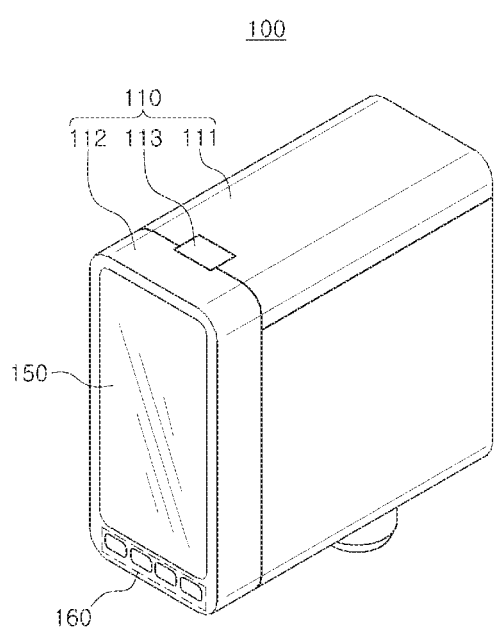
FIGS. 3 to 5 are perspective views illustrating an exterior of a gas detection device according to an exemplary embodiment.
Figure 4:
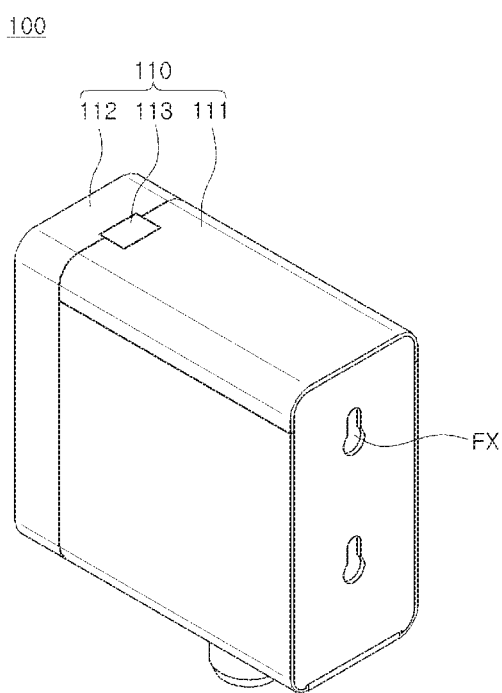
Figure 5:
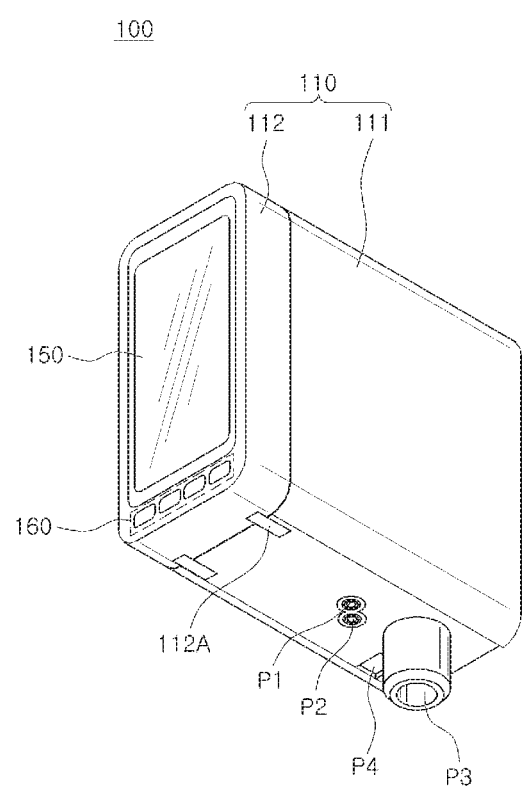

FIGS. 3 to 5 are perspective views illustrating an exterior of a gas detection device according to an exemplary embodiment.

With reference to FIG. 3, a gas detection device 100 according to an exemplary embodiment may include a case 110, a display 150, an input portion 160, and the like. A pump module drawing in and discharging air to detect a gas, a sensor module detecting a gas included in air drawn in, and a driving module driving the gas detection device 100 may be accommodated in the case 110.

The case 110 may include a main body 111 and a cover 112 coupled to the main body 111. The cover 112 may be provided on a front surface of the case 110. In an exemplary embodiment, the display 150 and the input portion 160 may be provided in the cover 112. The input portion 160 may include a plurality of mechanical input keys, or may include a touchscreen provided to be integrated with the display 150. The cover 112 may be coupled to the main body 111 by a hinge portion 113 and may allow an interior of the main body 111 to be exposed by being rotated around the hinge portion 113.

With reference to FIG. 4, the gas detection device 100 according to an exemplary embodiment may include a fixing portion FX provided on a rear surface of the case 110. The fixing portion FX may include a hole formed in the rear surface of the case 110 to a predetermined depth. A user may install an externally exposed ring, or the like, on a wall of a space or an apparatus in which the gas detection device 100 is disposed, thereby inserting the ring into the fixing portion FX to fix the gas detection device 100.

With reference to FIG. 5, the main body 111 and the cover 112 according to an exemplary embodiment may be coupled by a connection portion 112A. The connection portion 112A may be formed on a side of the cover 112 to allow the main body 111 to be connected and coupled to the cover 112 and to prevent the cover 112 from being opened during an operation of the gas detection device 100.

In the meantime, a plurality of ports P1 to P3 may be provided on a bottom surface of the case 110. In an exemplary embodiment, a first port P1 may be provided as an inlet port through which air is introduced, while a second port P2 may be provided as a discharge port through which air is discharged. Air introduced to the first port P1 may be discharged from the second port P2 through a sensor module mounted in the case 110. An amount of air introduced to the first port P1 and discharged from the second port P2 may be determined by the pump module mounted in the case 110.

In the meantime, the third port P3 may be provided as a cable gland and may be provided for receiving power from an external device or receiving a signal from an external controller. A fourth port P4 may be a Power-Over-Ethernet (PoE) Port. For example, the gas detection device 100 can communicate with an external controller, and/or receive a power for operation through the fourth port P4. According to an exemplary embodiment, additional ports may be further provided on an exterior of the case 110, in addition to the first to fourth ports P1 to P4.

Figure 6A:
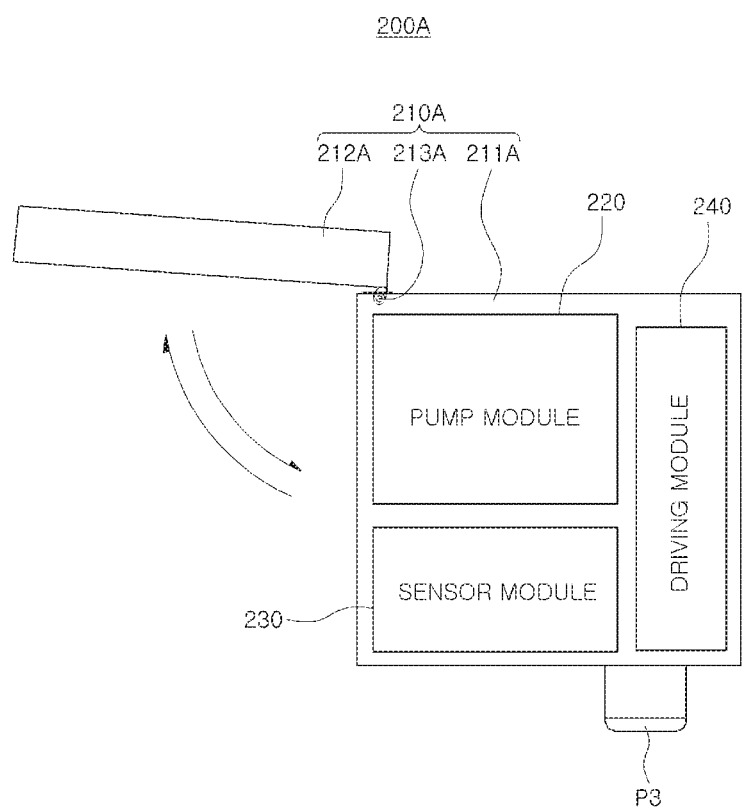
FIGS. 6A and 6B are views illustrating a gas detection device according to an exemplary embodiment.
Figure 6B:
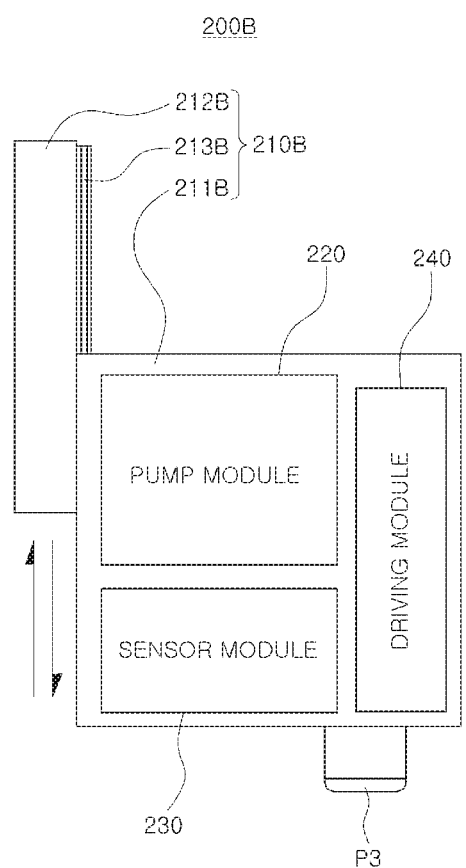

FIGS. 6A and 6B are views illustrating a gas detection device according to an exemplary embodiment.

In an exemplary embodiment illustrated in FIG. 6A, a gas detection device 200A may include a case 210A, a pump module 220 mounted in the case 210A, a sensor module 230, a driving module 240, and the like. In the meantime, a third port P3 provided as a cable gland may be provided on a bottom surface of the case 210A.

The case 210A may include a main body 211A and a cover 212A, as well as a hinge portion 213A connecting the main body 211A to the cover 212A. The cover 212A may be rotatably connected to the main body 211A by the hinge portion 213A. When the cover 212A is moved, the pump module 220, the sensor module 230, or the like, may be externally exposed. The pump module 220 and the sensor module 230 may be mounted in the main body 211A to be detachable therefrom. Thus, a user may open the cover 212A and may remove the pump module 220 or the sensor module 230 from the main body 211A to be extracted.

When the cover 212A is opened, front surfaces of the pump module 220 and the sensor module 230 may be externally exposed. In order for a user to easily remove the pump module 220 and the sensor module 230 from the main body 211A, the pump module 220 and the sensor module 230 may be fixed to the main body 211A using a member having elasticity. A user may remove the pump module 220 or the sensor module 230 from the main body 211A through only light pressure on the pump module 220 or the sensor module 230. In the meantime, the pump module 220 may have a volume greater than that of the sensor module 230.

In an exemplary embodiment illustrated in FIG. 6B, the gas detection device 200B may include a pump module 220, a sensor module 230, a driving module 240, and the like, mounted in the case 210B. A third port P3, provided as a cable gland, may be provided on a bottom surface of the case 210B.

The case 210B may include a main body 211B providing a space in which the pump module 220, the sensor module 230, and the driving module 240 are mounted and may include a cover 212B coupled to the main body 211B. The cover 212B may be coupled to the main body 211B to be movable in a sliding manner and may include a slide portion 213B so that the cover 212B may be coupled thereto to be moved in a sliding manner. In an exemplary embodiment, the cover 212B may be slidably moved in a direction of an upper portion of the main body 211B to allow the pump module 220 or the sensor module 230 to be externally exposed.

Figure 7:
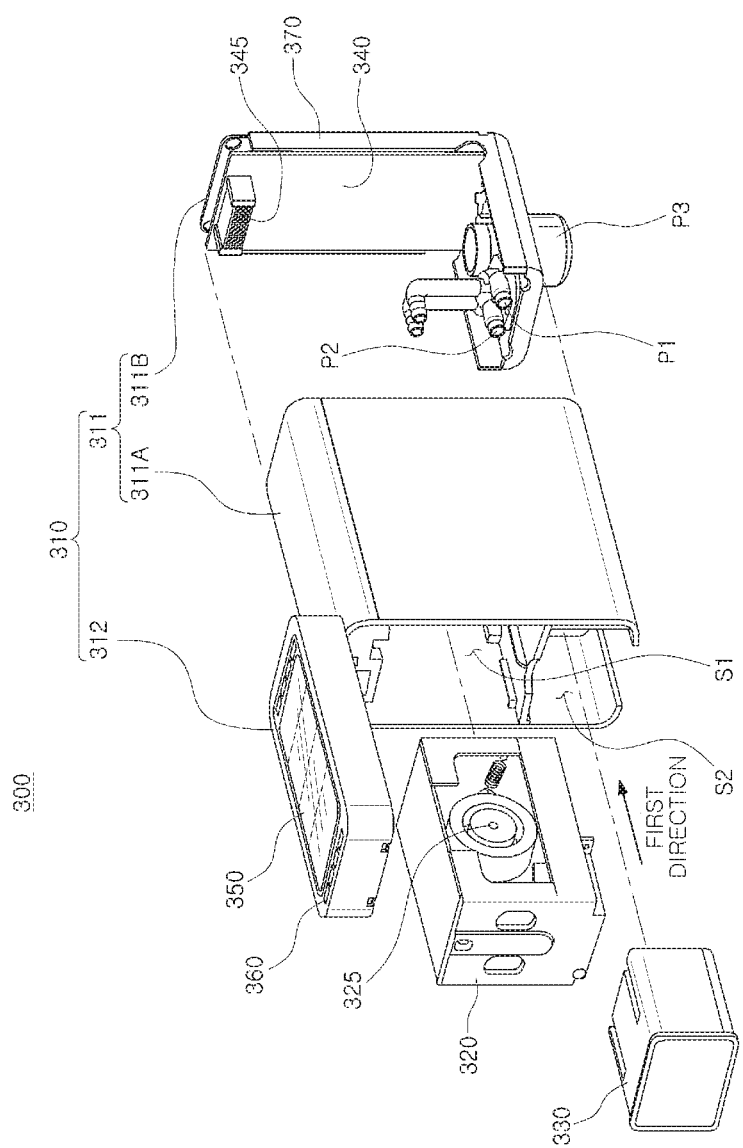
FIG. 7 is an exploded view of a gas detection device according to an exemplary embodiment.

FIG. 7 is an exploded view of a gas detection device according to an exemplary embodiment.

With reference to FIG. 7, a gas detection device 300 according to an exemplary embodiment may include a case 310, a pump module 320, a sensor module 330, a driving module 340, and the like.

The case 310 may include a main body 311 having a first frame 311A and a second frame 311B, as well as a cover 312. The first frame 311A and the cover 312 may be connected to each other by a connection member, such as a hinge portion. An interior of the first frame 311A may be covered or exposed by an opening and closing operation of the cover 312. The second frame 311B may be coupled to the first frame 311A by a coupling member, such as a screw, and may provide a rear surface and a bottom surface of the main body 311.

A plurality of ports P1 to P3 may be provided on a lower surface of the second frame 311B. In an exemplary embodiment, a first port P1 and a second port P2 may be provided as an inlet port and a discharge port of air, respectively. A pump pipe 370 connected to the pump module 320 may be provided in the second frame 311B. The pump module 320 may draw in air through the pump pipe 370, so that the air may be supplied to the sensor module 330. A pump 325 can be fixed by an elastic member, for example a spring, in the pump module 320. A permanent magnet can be included in the pump 325, and the pump 325 may be operated by electrical signal flowing through a coil provided adjacent to the permanent magnet.

In the meantime, the driving module 340 may be mounted in the second frame 311B. The driving module 340 may be coupled to the second frame 311B by a coupling member, such as a screw, or the like and may be connected to the pump module 320 or the sensor module 330 by a terminal 345 having a plurality of pins. The driving module 340 may supply driving power to the pump module 320 and the sensor module 330 and may control an operation of the pump module 320 and the sensor module 330. In an exemplary embodiment, the driving module 340 may control the pump module 320 to adjust an amount of air flowing into the sensor module 330, while the driving module 340 may output a type and a concentration of gases detected by the sensor module 330 to a display device 350. A user may transmit various commands to the driving module 340 by an input portion 360 or an external controller connected to the gas detection device 300.

The pump module 320 and the sensor module 330 may be mounted in the main body 311 so as to be detachable. The pump module 320 and the sensor module 330 may be mounted in a first accommodation space S1 and a second accommodation space S2 provided in the main body 311, respectively. In an exemplary embodiment, the driving module 340 may be disposed on a rear of the first accommodation space S1 and the second accommodation space S2. The pump module 320 and the sensor module 330 may be electrically connected to the driving module 340 in the first accommodation space S1 and the second accommodation space S2, respectively.

The pump module 320 and the sensor module 330 may be mounted in the first accommodation space S1 and the second accommodation space S2, respectively, in a sliding manner in a first direction. In addition, the pump module 320 and the sensor module 330 may be slidably removed from the main body 311 in the first direction to be extracted. When the gas detection device 300 is not normally operated, or regular management work is required, a user may open the cover 312 to easily remove the pump module 320 and the sensor module 330 from the main body 311. Thus, it is possible to efficiently manage the gas detection device 300. When either the pump module 320 or the sensor module 330 malfunctions, only a module that is malfunctioning may be replaced, thereby reducing repair costs and time.

Figure 8:
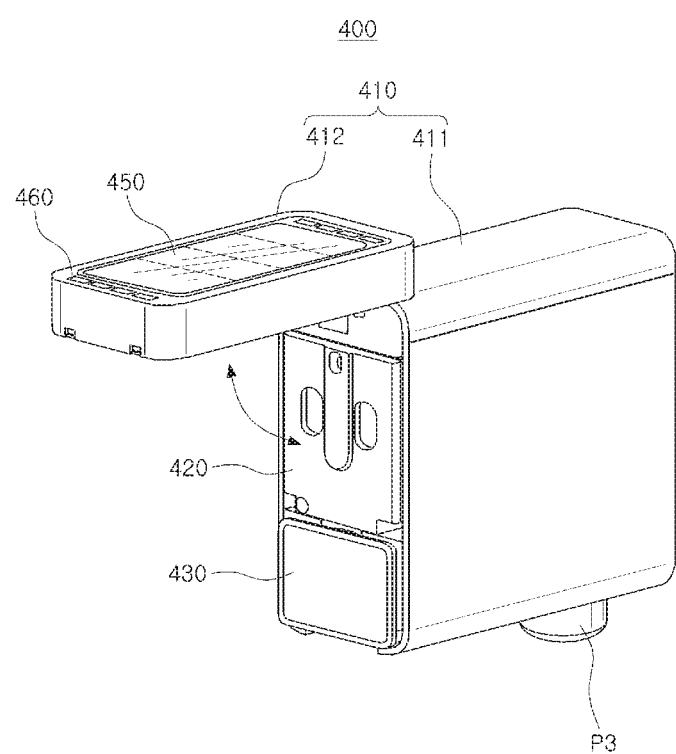
FIGS. 8 and 9 are views illustrating a gas detection device according to an exemplary embodiment.
Figure 9:
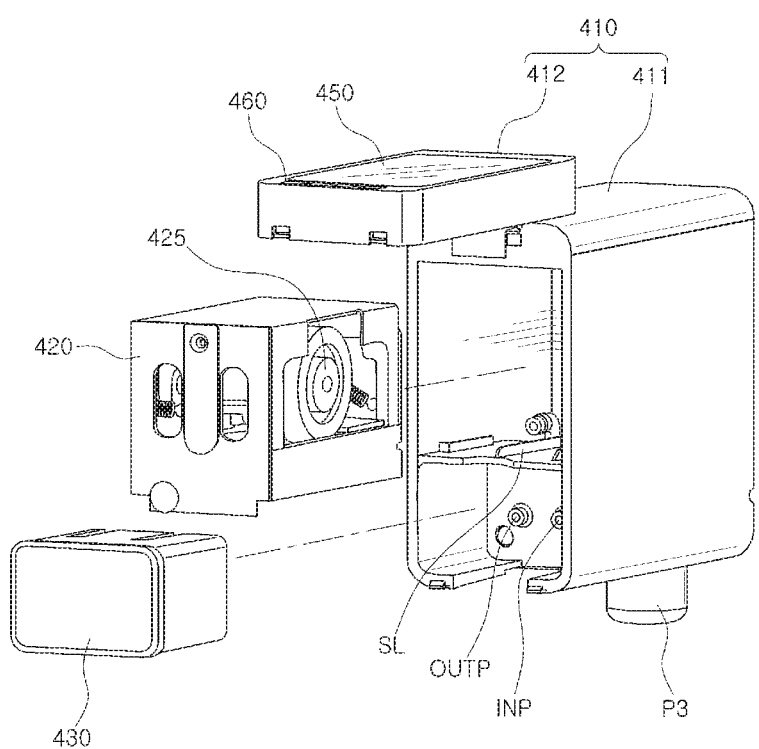

FIGS. 8 and 9 are views illustrating a gas detection device according to an exemplary embodiment.

With reference to FIG. 8, a gas detection device 400 according to an exemplary embodiment may include a case 410, a pump module 420, a sensor module 430, and the like. As illustrated in FIG. 8, the case 410 may include a main body 411 and a cover 412, while the cover 412 may be coupled to the main body 411 so as to be moved around the main body 411. In an exemplary embodiment illustrated in FIG. 8, when the cover 412 is opened, the pump module 420 and the sensor module 430 mounted in the main body 411 may be externally exposed.

Subsequently, with reference to FIG. 9, the pump module 420 and the sensor module 430 may be detachable from the main body 411 in a sliding manner. A slide member SL enabling the pump module 420 or the sensor module 430 to be moved in a sliding manner may be provided in the main body 411. For example, a user can remove the pump module 420 from the main body 411 by pulling the pump module 420 using a protrusion or hole on the front surface of the pump module 420. Therefore, without an additional equipment, the user can easily replace or repair the pump module 420 or the sensor module 430 by separating the pump module 420 or the sensor module 430 from the main body 411 by hand.

An inlet INP supplying air to the sensor module 430 and an outlet OUTP discharging air circulated in the sensor module 430 may be connected to the sensor module 430 and provided in the main body 411. The inlet INP and the outlet OUTP may be connected to an inlet and an outlet provided on a rear of the sensor module 430, respectively In the meantime, a pipe 475 connected to the pump module 420 may be provided in the main body 411. The pump module 420 may include a pump 425 connected to the pipe 475 to draw in external air into the gas detection device 400. The air drawn in by an operation of the pump module 420 may flow into the sensor module 430 through the inlet INP and may be circulated in the sensor module 430 to be discharged from the outlet OUTP.

Figure 10A:
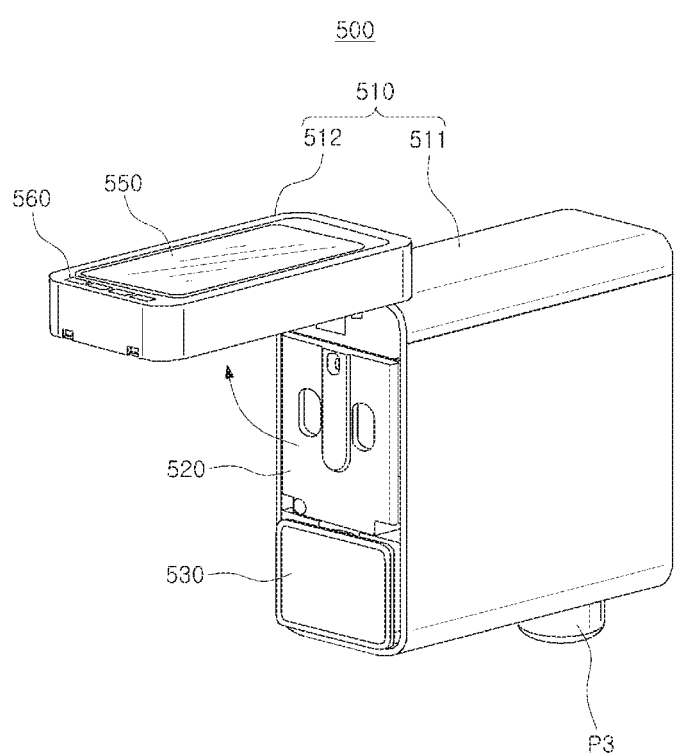
FIGS. 10A to 10C are views illustrating a method of replacing a sensor module in a gas detection device according to an exemplary embodiment.
Figure 10B:
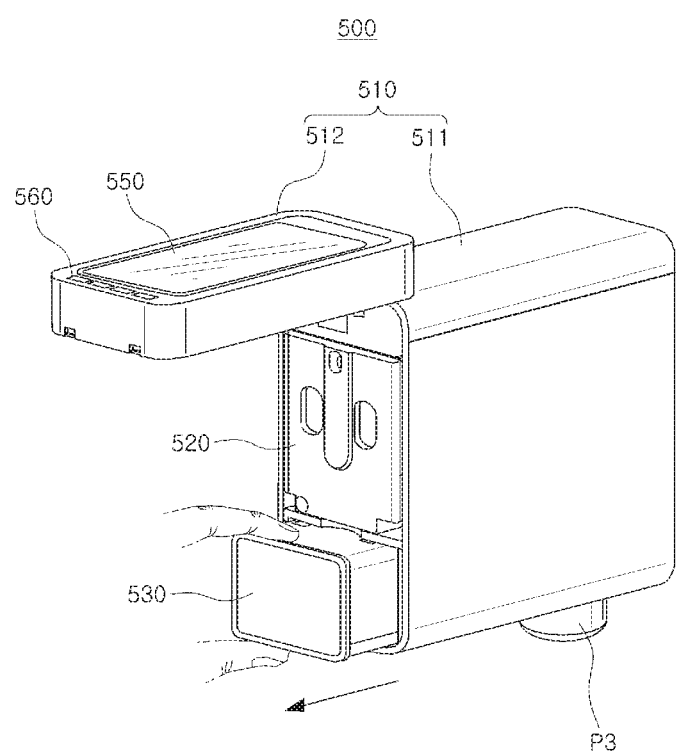
Figure 10C:
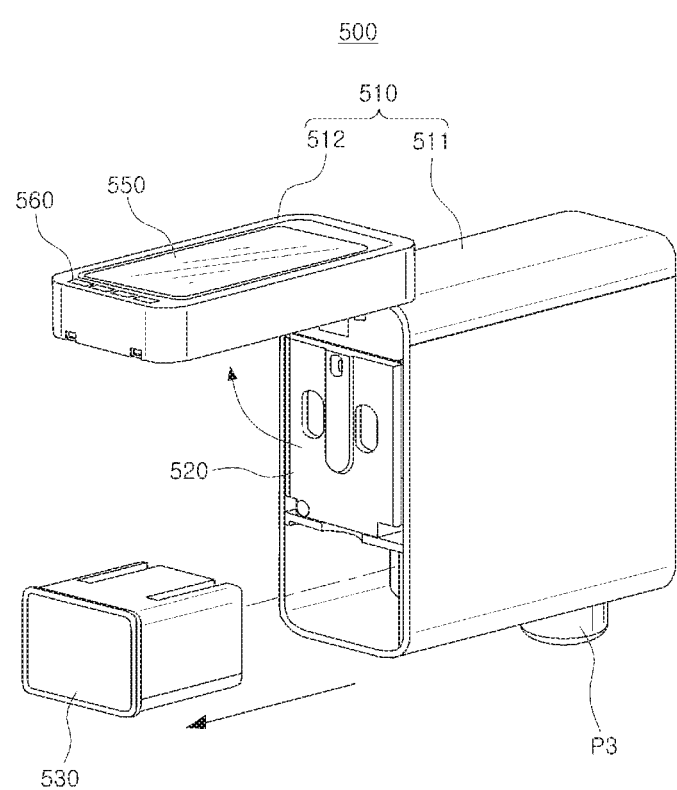

FIGS. 10A to 10C are views illustrating a method of replacing a sensor module in a gas detection device according to an exemplary embodiment.

With reference to FIG. 10A, a cover 512 may be opened to replace a sensor module 530. In an exemplary embodiment illustrated in FIG. 10A, the cover 512 is illustrated being opened by a hinge portion provided on an upper surface of a main body 511, but the present disclosure is not limited thereto. In another exemplary embodiment, the cover 512 may be opened by the hinge portion provided on a side surface or a lower surface of the main body 511, or may be opened by being slidably moved.

Subsequently, with reference to FIGS. 10B and 10C, in a state in which the cover 512 is opened, a user may remove only the sensor module 530 from the main body 511. In an exemplary embodiment, the sensor module 530 may include a plurality of unit sensors capable of detecting different gases. For example, the sensor module 530 may include a first unit sensor detecting silane gas (SiH4), a second unit sensor detecting hydrogen fluoride (PH3), a third unit sensor detecting ammonia, and a fourth unit sensor detecting hydrogen (H2).

A user may remove the sensor module 530 from the main body 511, in a case in which the sensor module 530 or one of the unit sensors malfunctions or in a case in which at least a portion of the unit sensors is to be replaced with another unit sensor. For example, a user may replace the first unit sensor detecting silane gas (SiH4) with a fifth unit sensor detecting boron trifluoride (BF3). As such, in the gas detection device 500 according to an exemplary embodiment, a user may easily replace the unit sensors included in the sensor module 530 or an entirety of the sensor module 530 according to need. Thus, efficiency of management and maintenance of the gas detection device 500 may be maximized.

In an exemplary embodiment, a front surface of the sensor module 530 may protrude further than a front surface of the pump module 520 and may be disposed below the pump module 520. The sensor module 530 may be more easily replaced than the pump module 520 from a structure described above. Referring to FIG. 10B, the user can pull the sensor module 530 projected forward from the pump module 530 with a finger and remove the sensor module 530 from the main body 511. This may be due to characteristics of the sensor module 530, in that the sensor module 530 may be removed from the main body 511 more frequently than the pump module 520, due to replacement of a unit sensor, inspection of a module, or the like. Thus, the sensor module 530 may be more conveniently removed from the main body 511.

Figure 11A:
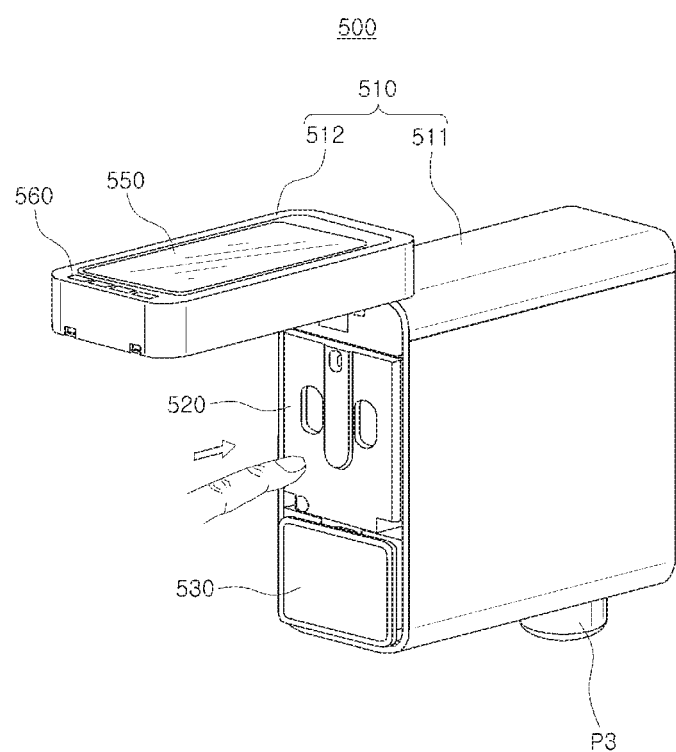
FIGS. 11A to 11C are views illustrating a method of replacing a pump module in a gas detection device according to an exemplary embodiment.
Figure 11B:
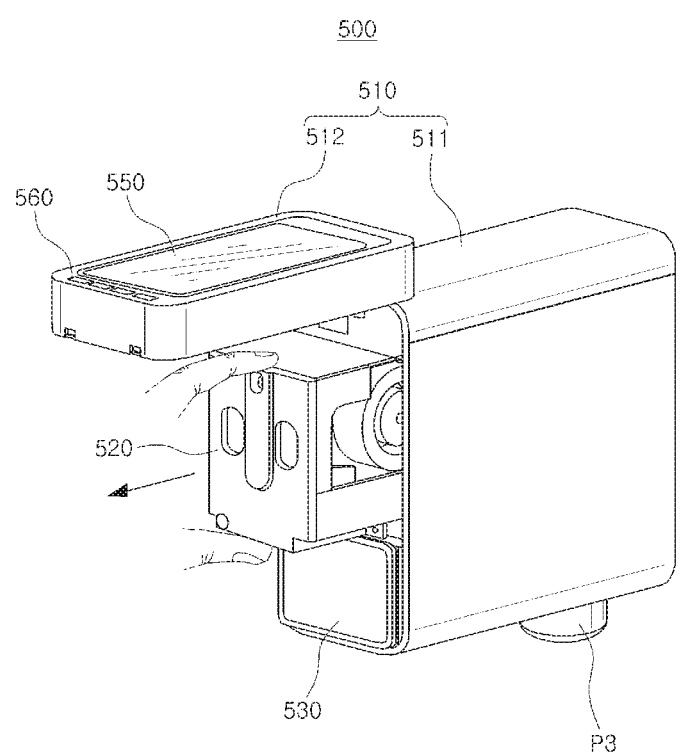
Figure 11C:
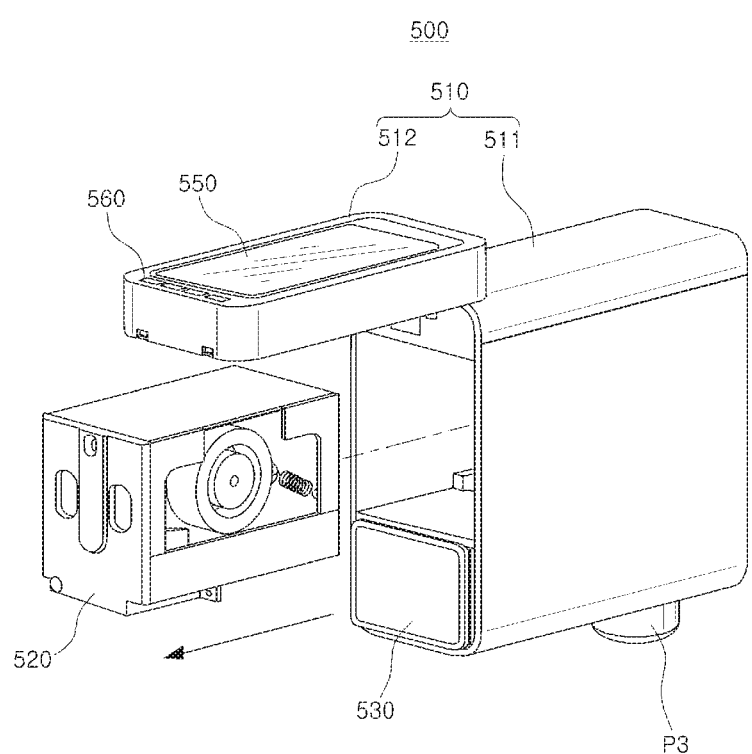

FIGS. 11A to 11C are views illustrating a method of replacing a pump module in a gas detection device according to an exemplary embodiment.

With reference to FIG. 11A, a cover 512 may be opened to replace a pump module 520. In an exemplary embodiment illustrated in FIG. 11A, the cover 512 is illustrated as being opened by a hinge portion provided on an upper surface of a main body 511, but the present disclosure is not limited thereto. In another exemplary embodiment, the cover 512 may be opened by the hinge portion provided on a side surface or a lower surface of the main body 511, or may be opened by being slidably moved.

Subsequently, with reference to FIGS. 11B and 11C, the pump module 520 may be removed from the main body 511. In an exemplary embodiment, the pump module 520 may be coupled to the main body 511 by an elastic member, such as a spring. The pump module 520 may protrude from an accommodation space of the main body 511 by applying force in a direction toward an interior of the body 511 to the pump module 520. Subsequently, a user may extract the pump module 520 to completely separate the pump module 520 from the main body 511.

In the meantime, a removal process of a sensor module 530 described with reference to FIGS. 10A to 10C may be applied to a removal process of the pump module 520, or a removal process of the pump module 520 described with reference to FIGS. 11A to 11C may be applied to the removal process of the sensor module 530.

Figure 12A:
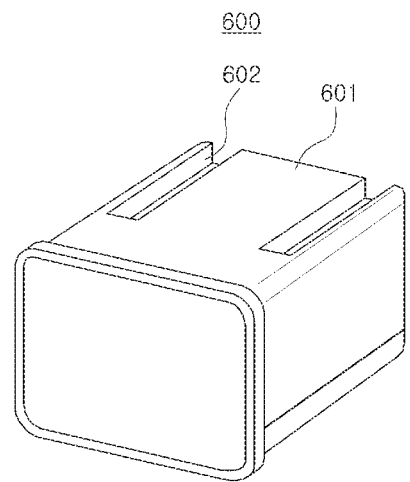
FIGS. 12A and 12B are views illustrating an exterior of the sensor module included in a gas detection device according to an exemplary embodiment.
Figure 12B:
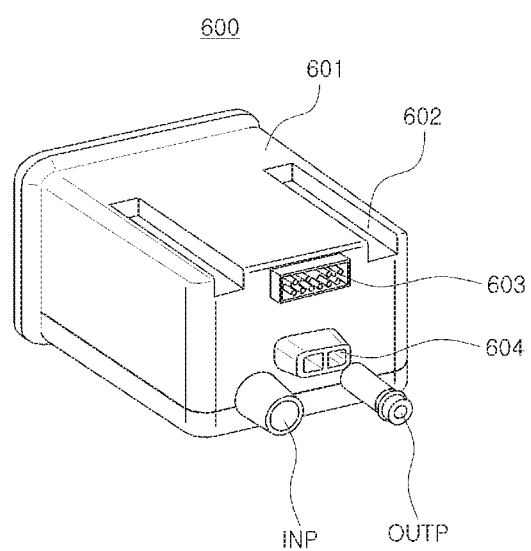

FIGS. 12A and 12B are views illustrating an exterior of the sensor module included in a gas detection device according to an exemplary embodiment.

With reference to FIGS. 12A and 12B, a sensor module 600 according to an exemplary embodiment may include a slide coupling portion 602 provided on a surface of a case 601 to be coupled to a main body of a gas detection device, an inlet INP providing an intake path of air, and an outlet OUTP providing a discharge path of air. In an examplary embodiment, a diameter of the outlet OUTP and a diameter of the inlet INP can be different from each other, in order to ensure a flow of air.

In the meantime, a terminal 603 required for connecting a driving module of the gas detection device to the sensor module 600 may be provided on a rear surface of the case 601. Also, a fixing portion 604 required for fixing the sensor module 600 to a main body of the gas detection device may be provided on the rear surface of the case 601. Unit sensors included in the sensor module 600 may receive power required for driving by the terminal 603, while the unit sensors may transmit a gas detection result to the driving module through the terminal 603.

Figure 13:
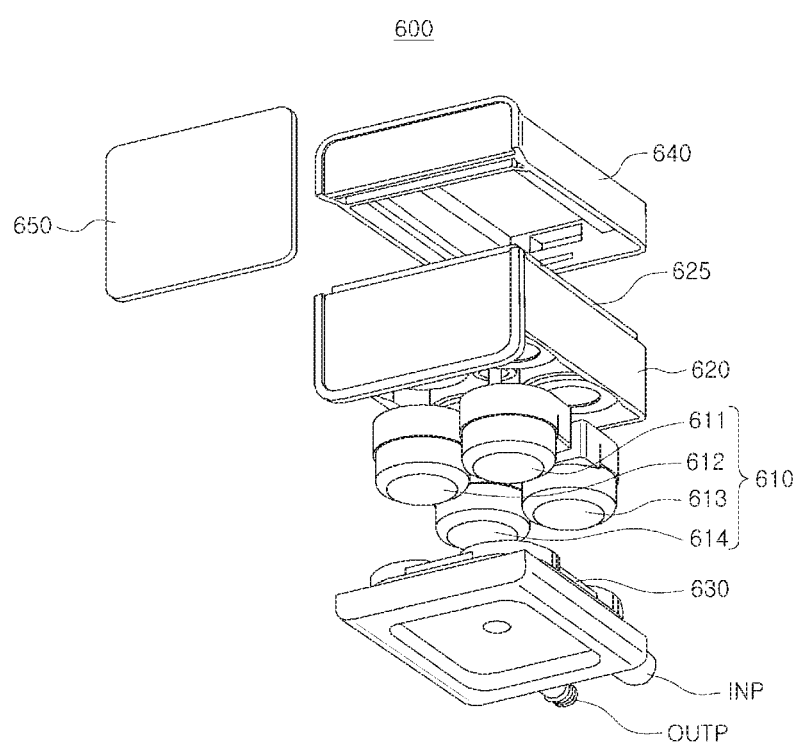
FIG. 13 is an exploded view illustrating the sensor module included in a gas detection device according to an exemplary embodiment.

FIG. 13 is an exploded view illustrating the sensor module included in a gas detection device according to an exemplary embodiment.

With reference to FIG. 13, a sensor module 600 according to an exemplary embodiment may include a sensor unit 610, a first housing 620, a second housing 630, a third housing 640, and a plate 650, and the like. The first housing 620, the second housing 630, and the third housing 640 may provide a sensor housing required to configure the sensor module 600.

The sensor unit 610 may include first to fourth unit sensors 611 to 614. According to an exemplary embodiment, the number of unit sensors 611 to 614, included in the sensor unit 610 may be variously changed. Each of the unit sensors 611 to 614 may include a gas cell detecting a gas, a sensor substrate on which the gas cell is mounted, an adapter, and the like. The unit sensors 611 to 614 may be mounted on the first housing 620. In this process, a module substrate 625 provided on the first housing 620 may be naturally connected to the adapter of the unit sensors 611 to 614. Thus, a user may simply change a type of a gas detected by the gas detection device in such a manner that the sensor module 600 is removed from the gas detection device, and then at least a portion among the unit sensors 611 to 614 is replaced with another unit sensor.

In the meantime, a non-volatile memory element may be provided on the sensor substrate of each of the unit sensors 611 to 614. In an exemplary embodiment, the non-volatile memory element may be provided as an electrically erasable programmable read only memory (EEPROM). Information on the gas cell included in each of the unit sensors 611 to 614 and parameter information needed for an operation thereof may be stored in the non-volatile memory element. In a case in which the unit sensors 611 to 614 are mounted on the first housing 620 to be connected to the module substrate 625, the information stored in the non-volatile memory element may be transferred to a driving module of the gas detection device, or the like, by the module substrate 625. The driving module may control the unit sensors 611 to 614 based on the information stored in the non-volatile memory element.

The second housing 630 may be provided below the sensor unit 610. A hole corresponding to each of the unit sensors 611 to 614 may be formed in the second housing 630, while an inlet INP drawing in air and an outlet OUTP discharging air may be provided therein. The second housing 630 may be coupled to the first housing 620. In an exemplary embodiment, a protruding portion for guiding a flow of air to the sensor unit 610 may be formed on an upper surface of the second housing 630, which will be subsequently described with reference to FIG. 14.

The third housing 640 may be provided on the first housing 620. The third housing 640 may cover the module substrate 625 so that the module substrate 625 may not be externally exposed. The third housing 640 may include a slide coupling portion 602, as illustrated in FIGS. 12A and 12B. In a case in which the first housing 620, the second housing 630, and the third housing 640 are coupled, the plate 650 may be attached to a front surface thereof, and the first housing 620, the second housing 630, the third housing 640, and the plate 650 may be provided as a case 601.

Figure 14A:
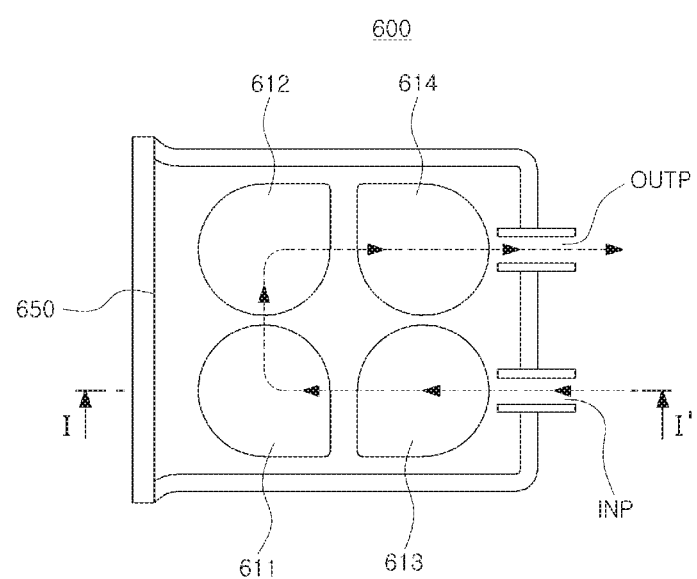
FIGS. 14A and 14B are views illustrating a flow of air in the sensor module according to an exemplary embodiment.
Figure 14B:
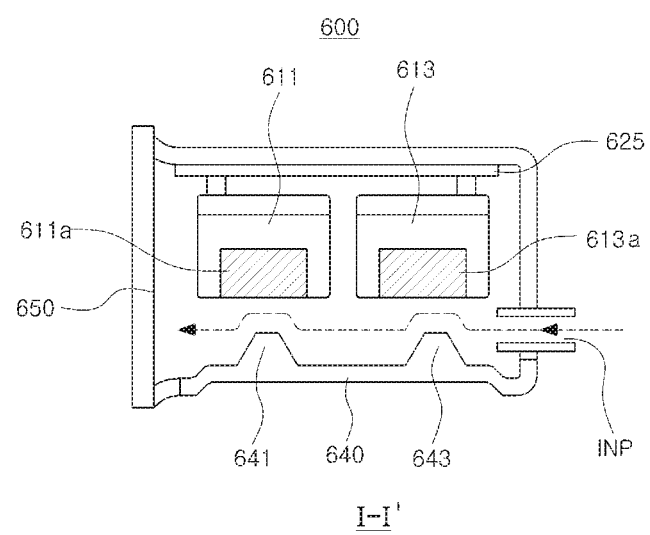

FIGS. 14A and 14B are views illustrating a flow of air in the sensor module according to an exemplary embodiment.

FIG. 14A may be provided as a top view illustrating at least a portion of components included in a sensor module 600. With reference to FIG. 14A, the sensor module 600 according to an exemplary embodiment may include a plurality of unit sensors 611 to 614. In addition, air introduced through an inlet INP may flow through unit sensors 611 to 614 to be discharged from an outlet OUTP. The unit sensors 611 to 614 may be mounted on a module substrate 625, detect a gas included in the air introduced through the inlet INP, and transfer the result to a driving module of a gas detection device by the module substrate 625.

The air introduced through the inlet INP may flow sequentially through the unit sensors 611 to 614 to be discharged from the outlet OUTP. In other words, the unit sensors 611 to 614 may be disposed in series along a path of air flowing into the inlet INP and discharged from the outlet OUTP.

FIG. 14B is a cross-sectional view taken along line I-I' of FIG. 14A. With reference to FIG. 14B, the sensor module 600 according to an exemplary embodiment may include a second housing 630 disposed below the unit sensors 611 to 614. The second housing 630 may be disposed adjacent to a gas cell included in each of the unit sensors 611 to 614 and may include a plurality of protruding portions 641 and 643, protruding toward the unit sensors 611 to 614. A direction of the air introduced to the inlet INP may be changed to be adjacent to the gas cell by the protruding portions 641 and 643 and may increase a gas detection probability and accuracy of the sensor module.

In the meantime, in the same manner as an exemplary embodiment illustrated in FIG. 14B, each of the unit sensors 611 to 614 may include a detection cell including an electrolyte to detect a gas, or the like. In an exemplary embodiment, the gas detection device may be disposed so that a gas detection surface defined as a surface of the detection cell included in the unit cells 611 to 614 may be oriented in a direction of the ground. Thus, the electrolyte included in the detection cell may be naturally concentrated toward the gas detection surface by gravity, thereby improving gas detection performance.

Figure 15:
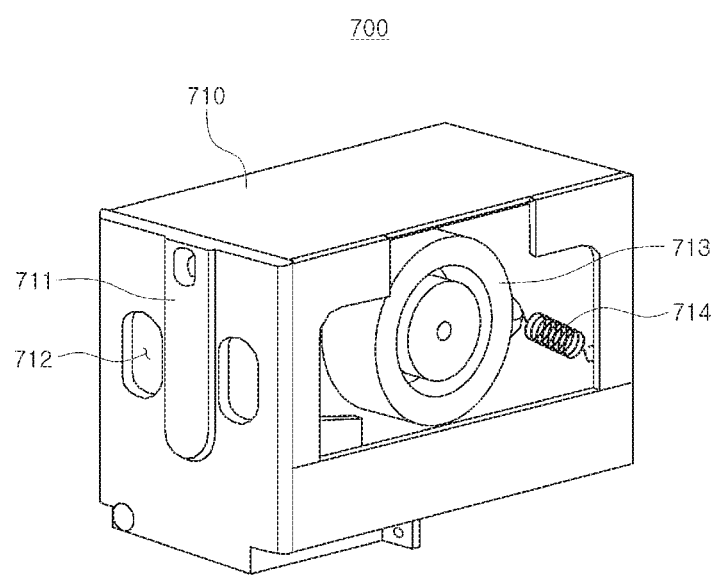
FIG. 15 is a view illustrating the pump module included in a gas detection device according to an exemplary embodiment.

FIG. 15 is a view illustrating the pump module included in a gas detection device according to an exemplary embodiment.

Referring to FIG. 15, a pump module 700 may include a case 710, a protrusion 711 and a hole 712 provided on a front surface of the case 710, a pump 713 included in the case 710, and an elastic member 714 for fixing the pump 713. The pump module 700 may be removably included in the gas detection device.

In an exemplary embodiment, at least a portion of a case of the gas detection device may be opened to expose the pump module 700, and the pump module 700 may be separated from the gas detection device for repair or replacement with a new module. In an exemplary embodiment, a user can remove the pump module 700 from the gas detection device, without any additional equipment. The protrusion 711 or the hole 712 on the front surface of the case 710, may be provided for easy separation of the pump module. The user can easily separate the pump module 700 from the gas detection device without any additional tool or equipment by pulling the pump module 700 using the protrusion 711 or the hole 712.

The pump 713 can be included in the case 710 in a state of being fixed by the elastic member 714. In an examplary embodiment, the pump 713 is fixed inside the case 710 by a plurality of elastic members 714, and may not be contact with the inner wall of the case 710. In the pump 713, a permanent magnet may be provided, and at least one coil may be provided in the case 710 so as to be adjacent to the permanent magnet. When electric signal is supplied to the coil of the case 710, the pump 713 vibrates due to the magnetic force from the magnetic field between the coil and the permanent magnet, and the pump 713 can draw an air from outside.

As set forth above, according to exemplary embodiments in the present disclosure, a gas detection device may allow a pump module and a sensor module, mounted in a main body, to be easily replaced and repaired using a cover provided to expose an interior of the main body, so that efficient maintenance thereof is possible. In addition, since unit sensors included in the sensor module or the pump module may be easily replaced, the gas detection device may be easily reconfigured based on specifications in accordance with a user's purpose.

While exemplary embodiments have been shown and described above, it will be apparent to those skilled in the art that modifications and variations could be made without departing from the scope of the present invention as defined by the appended claims.

This application claims priority of Korean Patent Application No. 10-2017-0120286 filed on Sep. 19, 2017, which is hereby incorporated herein by reference.

What is claimed is:

1. A gas detection device, comprising:
   a pump for drawing in air and a pump case housing the pump;
   a sensor housing and a plurality of unit sensors mounted in the sensor housing and configured to detect a plurality of gases included in the air;
   a controller for driving the pump and the plurality of unit sensors; and
   a case including a main body in which at least one among the pump case, the sensor housing, and the controller is mounted to be detachable and a cover connected to the main body to allow the at least one among the pump case, the sensor housing, and the controller to be exposed,
   wherein the pump case and the sensor housing are able to be moved in a first direction, and wherein the main body comprises an elastic member pushing the pump case and the sensor housing in a direction opposite to the first direction when force is applied in the first direction.

2. The gas detection device of claim 1, wherein the case comprises a hinge portion connecting the cover to the main body.

3. The gas detection device of claim 1, wherein the case comprises a slide portion connecting the cover to the main body.

4. The gas detection device of claim 1, wherein the pump case and the sensor housing are exposed based on removal of the cover.

5. The gas detection device of claim 4, wherein the pump case and the sensor housing are mounted in at least one accommodation space provided in the main body to be detachable from the main body.

6. The gas detection device of claim 5, wherein the pump case and the sensor housing are mounted in the at least one accommodation space in a sliding manner.

7. The gas detection device of claim 1, further comprising an input portion for receiving an input from a user; and a display for displaying a state of at least one among the pump, the plurality of unit sensors and a gas detection result of the plurality of unit sensors.

8. The gas detection device of claim 7, wherein the input portion and the display are provided in the cover.

9. The gas detection device of claim 1, further comprising a module substrate in which a circuit processing an electrical signal generated by the plurality of unit sensors and a terminal outputting the electrical signal are formed, and wherein the module substrate is mounted in the sensor housing, the plurality of unit sensors being detachable from the sensor housing.

10. The gas detection device of claim 9, wherein the sensor housing comprises a protruding portion disposed adjacent to a detection surface of the plurality of unit sensors and protruding in a direction toward the detection surface to allow the air to flow in the direction toward the detection surface.

11. The gas detection device of claim 1, wherein the plurality of unit sensors comprise a first unit sensor, a second unit sensor, a third unit sensor, and a fourth unit sensor, and the first unit sensor, the second unit sensor, the third unit sensor, and the fourth unit sensor have the same size and shape.

12. The gas detection device of claim 1, wherein the case comprises a first port providing an intake path of the air and a second port providing a discharge path of the air.

13. The gas detection device of claim 12, wherein the plurality of unit sensors are disposed in series along a path of air introduced to the first port to be discharged from the second port.

14. The gas detection device of claim 1, wherein the main body provides a first accommodation space in which the pump case is mounted and a second accommodation space in which the sensor housing is mounted, and the first accommodation space and the second accommodation space are disposed between the controller and the cover.

15. The gas detection device of claim 1, wherein each of the plurality of unit sensors is disposed in the sensor housing to allow a detection surface in contact with the gas to face the ground.

16. A gas detection device, comprising:
   a case including a main body having a first accommodation space and a second accommodation space and a cover rotatably connected to the main body to allow the first accommodation space and the second accommodation space to be opened and closed;
   a pump and a pump case housing the pump, wherein the pump case is mounted in the first accommodation space to be detachable and insertable in a sliding manner and the pump draws in air;
   a sensor housing and a plurality of unit sensors mounted in the sensor housing, wherein the sensor housing is mounted in the second accommodation space to be detachable and insertable in a sliding manner and the plurality of unit sensors detect a plurality of gases included in the air; and
   a controller provided on a rear of the first accommodation space and the second accommodation space and driving the pump and the plurality of unit sensors,
   wherein the pump case and the sensor housing are able to be moved in a first direction, and wherein the main body comprises an elastic member pushing the pump case and the sensor housing in a direction opposite to the first direction when force is applied in the first direction.

17. The gas detection device of claim 16, wherein the case comprises a first port provided on a first surface of the main body and drawing in the air, wherein the first surface is disposed in a lower portion of the second accommodation space, a second port provided on the first surface of the main body and discharging the air, and a third port provided on the first surface of the main body.

18. The gas detection device of claim 16, wherein the case comprises a fixing portion provided on a rear surface of the main body and fixing the main body to at least one of an external apparatus and an external wall, wherein the rear surface is disposed on a rear of the controller.

19. The gas detection device of claim 16, wherein the cover is connected to the main body to be able to be rotated around a horizontal rotational axis by a hinge portion provided on an upper surface of the main body.

* * * * *